United States Patent [19]

Knifton

[11] Patent Number: 4,540,810

[45] Date of Patent: * Sep. 10, 1985

[54] MANUFACTURE OF ALKANOL AND GLYCOL ESTERS

[75] Inventor: John F. Knifton, Austin, Tex.

[73] Assignee: Texaco Development Corporation, Bellaire, Tex.

[*] Notice: The portion of the term of this patent subsequent to May 5, 1998 has been disclaimed.

[21] Appl. No.: 77,419

[22] Filed: Sep. 20, 1979

[51] Int. Cl.$^3$ .................. C07C 67/36; C07C 69/003
[52] U.S. Cl. .................. 560/226; 260/399; 260/404; 260/404.5; 260/408; 260/410.6; 260/410.9 R; 260/465.4; 560/1; 560/19; 560/50; 560/100; 560/103; 560/105; 560/112; 560/122; 560/123; 560/124; 560/127; 560/152; 560/155; 560/178; 560/186; 560/187; 560/190; 560/198; 560/204; 560/227; 560/230; 560/263; 560/265; 546/321; 546/327; 549/484
[58] Field of Search ............... 560/230, 263, 227, 226, 560/198, 187, 186, 178, 155, 265, 204, 152, 190; 260/410.6, 410.9 R, 465.4, 404, 408, 399, 404.5

[56] References Cited

U.S. PATENT DOCUMENTS

| | | | |
|---|---|---|---|
| 2,534,018 | 12/1950 | Gresham et al. | 560/263 |
| 2,549,470 | 4/1951 | Howk et al. | 568/902 |
| 2,632,014 | 3/1953 | Gresham | 260/449 R |
| 3,040,090 | 6/1962 | Alderson | 568/902 |
| 3,767,709 | 10/1973 | Fenton | 568/902 |
| 3,878,290 | 4/1975 | Walker et al. | 423/417 |
| 3,944,588 | 3/1976 | Kaplan | 260/449 R |
| 4,013,700 | 3/1977 | Cawse | 260/449 R |
| 4,098,727 | 7/1978 | Haag et al. | 260/449 R |
| 4,265,828 | 5/1981 | Knifton | 518/700 |
| 4,268,689 | 5/1981 | Knifton | 560/265 |

FOREIGN PATENT DOCUMENTS 2644185  4/1977  Fed. Rep. of Germany ... 260/449 R

OTHER PUBLICATIONS

Picker et al., Brennstoff Chemie, No. 9, Bil 48, 1967, pp. 266–272.

*Primary Examiner*—Vivian Garner
*Attorney, Agent, or Firm*—Robert A. Kulason; James L. Bailey

[57] ABSTRACT

This invention concerns the improved preparation of alkanol and glycol esters, such as ethylene glycol diesters, by reaction of carbon monoxide and hydrogen in the presence of a catalyst system comprising ruthenium and a quaternary aryl or alkaryl phosphonium salt and a liquid phase medium containing a carboxylic acid coreactant.

20 Claims, No Drawings

MANUFACTURE OF ALKANOL AND GLYCOL ESTERS

SUMMARY AND BACKGROUND OF INVENTION

This invention concerns an improved process for preparing alkanol and vicinal glycol ester compounds, including ester derivatives of ethylene glycol, by reaction of oxides of carbon with hydrogen.

In copending, commonly assigned application Ser. No. 968,655, filed Dec. 11, 1978, now abandoned, the inventive process concerns the selective co-synthesis of alkanol and glycol esters, particularly the ester derivative of ethylene glycol, methanol and ethanol, by the catalytic reaction of carbon monoxide and hydrogen in the presence of a liquid medium containing a carboxylic acid co-reactant. Catalysis is effected in the presence of a catalyst containing osmium or ruthenium transition metals, in combination with specific classes of co-catalyst salt species. The process is exemplified by, but not limited to, the one step co-synthesis of ethylene glycol diacetate, methyl acetate and ethyl acetate from carbon monoxide, hydrogen mixtures—commonly known as synthesis gas—in the presence of an acetic acid (HOAc) liquid medium according to the stoichiometry of eqs. (1) to (3):

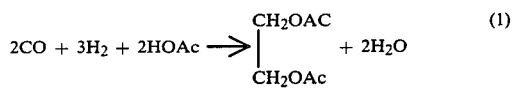

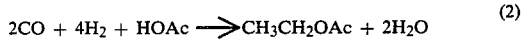

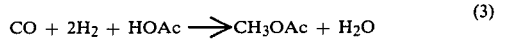

Methyl acetate, ethyl acetate and glycol diacetate are all products of recognized commercial value, particularly as chemical intermediates and extractive solvents. Methyl and ethyl acetates are used widely as solvents, primarily for surface coatings. Ethylene glycol diacetate is useful in the production of ethylene glycol, an important component in polyester fiber and antifreeze formulations. Free glycol may be generated from its diacetate derivative via hydrolysis, as disclosed, for example, in Belgium Pat. No. 749,685.

It is the purpose of this invention and that of the just mentioned companion case to provide new routes to the preparation of alkanol and diol esters using mixtures of carbon monoxide and hydrogen (commonly called synthesis gas or syngas) as the primary building block. This is particularly true where methyl acetate, ethyl acetate and glycol diacetate are the principal products (eqs. 1-3), since in this case acetic acid is the co-reactant media, and one route to HOAc manufacture is from synthesis gas via methanol carbonylation. ("Trends in Petrochemical Technology" by A. M. Brownstein, Chapter 5 (1976)).

In recent years, a large number of patents have been issued dealing with the synthesis of lower molecular weight hydrocarbons, olefins, alkanols etc. from synthesis gas. Of particular note, U.S. Pat. No. 2,636,046, discloses the synthesis of polyhydric alcohols and their derivatives by reaction between carbon monoxide and hydrogen at elevated pressures (>1500 atm of 22,000 psi) and temperatures to 400° C. using certain cobalt-containing catalysts. More recently, in Belgium Pat. No. 793,086 and U.S. Pat. No. 3,940,432 there is described the co-synthesis of methanol and ethylene glycol from mixtures of carbon monoxide and hydrogen using a rhodium complex catalyst. Typically, CO-hydrogenation is effected at 8000 psi of 1:1 $H_2/CO$ synthesis gas, at 220° C., using tetraglyme as the solvent, and dicarbonylacetylacetonatorhodium(I) in combination with an organic Lewis base as the catalyst precursor. (For summary of the work, see: R. L. Pruett, Annals New York Academy of Sciences, Vol. 295 p. 239 (1977)). While other metals of Group VIII of the Periodic Table have been tested for activity under similar conditions, including cobalt, ruthenium, copper, manganese, iridium and platinum, only cobalt was found to have slight activity. The use of ruthenium compounds in particular failed to produce polyfunctional products such as ethylene glycol. This is illustrated in U.S. Pat. No. 3,833,634 for solutions of triruthenium dodecacarbonyl.

PROCESS EMBODIMENTS

The present invention constitutes a still further improvement of the above mentioned pending application which in its broadest aspects involves preparation of alkanol and vicinal glycol esters from mixtures of carbon monoxide and hydrogen (synthesis gas) by contacting said synthesis gas with a catalyst containing a ruthenium transition metal and various co-catalyst salt species including quaternary aliphatic phosphonium salts and heating said reaction mixture under superatmospheric pressures until the desired esters are formed.

In the narrower and more preferred practice of that invention, methanol, ethanol and ethylene glycol esters are prepared concurrently from a synthesis gas mixture of carbon monoxide and hydrogen by a process comprising the following steps:

(a) Contacting said mixture of carbon monoxide and hydrogen with a liquid medium containing one or more aliphatic carboxylic acids and a ruthenium-containing catalyst and a co-catalyst salt species.

(b) Heating said reaction mixture to a temperature of between about 100° C. and 350° C., at superatmospheric pressures of 500 psi or greater with sufficient carbon monoxide and hydrogen to satisfy the stoichiometry of the desired ester synthesis, until substantial formation of the desired esters of methanol, ethanol and ethylene glycol has been achieved, and (c) Isolating said esters contained therein.

The improvements here involves the use, as a co-catalyst species, of an aryl or alkaryl phosphonium salt. Said salt containing an aryl moiety gives unexpected improved results as will be shown below.

In order to present the inventive concept in the greatest possible detail as to promote its understanding, the following supplementary disclosure is submitted. The basic invention, improved upon here is practiced as follows.

A. Catalyst Composition

Catalysts that are suitable in the practice of this invention contain a ruthenium transition metal. The ruthenium catalyst may be chosen from a wide variety of organic inorganic compounds, complexes, etc., as will be shown and illustrated below. It is only necessary that the catalyst precursor actually employed contain said transition metal in any of its ionic states. The actual catalytically active species is then believed to comprise ruthenium in complex combination with carbon monoxide and hydrogen. The most effective catalysis is achieved where the ruthenium hydrocarbonyl species is solubilized in the carboxylic acid co-reactant employed to satisfy the stoichiometry of eq 1-3.

The preferred ruthenium catalyst precursors may take many different forms. For instance, the ruthenium may be added to the reaction mixture in an oxide form, as in the case of, for example, ruthenium(IV) oxide, hydrate, anhydrous ruthenium(IV) dioxide, ruthenium-(IV) dioxide hydrate and ruthenium(VIII) tetraoxide. Alternatively, it may be added as the salt of a mineral acid, as in the case of ruthenium(III) chloride hydrate, ruthenium(III) bromide, anhydrous ruthenium(III) chloride and ruthenium nitrate, or as the salt of a suitable organic carboxylic acid (see Section B, below), for example, ruthenium(III) acetate, ruthenium(III) propionate, ruthenium butyrate, ruthenium(III) trifluoroacetate, ruthenium octanoate, ruthenium naphthenate, ruthenium(III) acetylacetonate and ruthenium hexafluoroacetylacetonate may also be employed. The ruthenium may also be added to the reaction zone as a carbonyl or hydrocarbonyl derivative. Here, suitable examples include triruthenium dodecacarbonyl, hydrocarbonyls such as $H_2Ru_4(CO)_{13}$ and $H_4Ru_4(CO)_{12}$, and substituted carbonyl species such as the tricarbonylruthenium(II) chloride dimer, $[Ru(CO)_3Cl_2]_2$.

In a preferred embodiment of the invention ruthenium is added to the reaction zone as one or more oxide, salt or carbonyl derivative species in combination with one or more Group VB tertiary donor ligands. The key elements of the Group VB ligands include nitrogen, phosphorous, arsenic and antimony. These elements, in their trivalent oxidation states, particularly tertiary phosphorus and nitrogen, may be bonded to one or more alkyl, cycloalkyl, aryl, substituted aryl, aryloxide, alkoxide and mixed alkaryl radicals, each containing from 1 to 12 carbon atoms, or they may be part of a heterocyclic ring system, or be mixtures thereof. Illustrative examples of suitable ligands that may be used in this invention include: triphenylphsophine, tri-n-butylphosphine, triphenylphosphite, triethylphosphite, trimethylphosphite, trimethylphosphine, tri-p-methoxyphenylphosphine, triethylphosphine, trimethylarsine, triphenylarsine, tri-p-tolylphosphine, tricyclohexylphosphine, dimethylphenylphosphine, trioctylphosphine, tri-o-tolylphosphine, 1,2-bis(diphenylphosphino)ethane, tri-phenylstibine, trimethylamine, triethylamine, tripropylamine, tri-n-octylamine, pyridine, 2,2'-dipyridyl, 1,10-phenanthroline, quinoline, N,N'-dimethylpiperazine, 1,8-bis(dimethylamino)naphthalene and N,N-dimethylaniline.

One or more of these ruthenium-tertiary Group VB donor ligand combinations may be preformed, prior to addition to the reaction zone, as in the case, for example, of tris(triphenylphosphine)ruthenium(II) chloride and tricarbonylbis(triphenylphosphine)ruthenium or alternatively, said complexes may be formed in situ.

The performances of each of these classes of ruthenium catalyst precursors are illustrated by the accompanying examples, described below.

B. Carboxylic Acids

Carboxylic acids useful in the process of this invention form the acid moiety of the desired methyl, ethyl and glycol ester products. Preferably, said acids are also useful as solvents for the transition-metal catalysts, particularly the ruthenium catalyst combinations. Suitable carboxylic acids include aliphatic acids, alicyclic monocarboxylic acids, heterocyclic acids and aromatic acids, both substituted and non-substituted. For example, this invention contemplates the use of lower mono aliphatic acids of 1 to 12 carbon atoms such as formic acid, acetic, propionic, butyric, isobutyric, valeric, caproic, capric, perlargonic and lauric acids, together with dialiphatic acids of 2 to 6 carbons, such as oxalic, malonic, succinic and adipic acids. The invention further contemplates the use of substituted monoaliphatic acids containing one or more functional substituents, such as the lower alkoxy, chloro, fluoro, cyano, alkylthio, and amino functional groups, examples of which include acetoacetic acid, dichloroacetic and trifluoroacetic acid, chloropropionic acid, trichloroacetic acid, monofluoroacetic acid and the like. Among the suitable aromatic acids contemplated are benzoic acid, naphthoic acids, toluic acids, chlorobenzoic acids, aminobenzoic acids and phenylacetic acid. The alicyclic monocarboxylic acids may contain from 3 to 6 carbons in the ring, both substituted and unsubstituted, and may contain one or more carboxyl groups, such as cyclopentanecarboxylic acid and hexahydrobenzoic acids. The heterocyclic acids may contain 1 to 3 fused rings both substituted and unsubstituted together with one or more carboxylic groups. Examples include quinolinic, furoic and picolinic acids. Mixtures of said classes of carboxylic acids, in any ratio, may also be used in the inventive process. The preferred carboxylic acids are the lower aliphatic acids such as acetic acid, propionic acid and butyric acid, together with substituted aliphatic acids such as trifluoroacetic acid.

C. Catalyst Concentration

The quantity of ruthenium catalyst employed in the instant invention is not critical and may vary over a wide range. In general, the novel process is desirably conducted in the presence of a catalytically effective quantity of the active ruthenium species which gives the desired ester products in reasonable yields. Reaction proceeds when employing as little as about $1 \times 10^{-6}$ weight percent, and even lesser amounts, of ruthenium, basis the total weight of the reaction mixture. The upper concentration is dictated by a variety of factors including catalyst cost, partial pressures of carbon monoxide and hydrogen, operating temperature and choice of carboxylic acid diluent/reactant. A ruthenium catalyst concentration of from about $1 \times 10^{-5}$ to about 10 weight percent ruthenium, based on the total weight of reaction mixture, is generally desirable in the practice of this invention.

D. Operating Temperature

The temperature range which can usefully be employed in these ester syntheses is a variable dependent upon other experimental factors, including the choice of carboxylic acid co-reactant, the pressure, and the concentration and particular form of catalyst among other things. Usually, the range of operability is from about 100° to 350° C. when superatmospheric pressures of syngas are employed. A narrower range of 150°-260° C. represents the preferred temperature range when the major products are methyl, ethyl and glycol acetates.

E. Pressure

Superatmospheric pressures of 500 psi or greater lead to substantial yield of desirable alkanol and vicinal glycol ester by the process of this invention. A preferred operating range for solutions of ruthenium(III) acetylacetonate in acetic acid is from 1000 psi to 7500 psi, although pressures above 7500 psi also provide useful yields of desired ester. The pressures referred to here represent the total pressure generated by all the reactants, although they are substantially due to the carbon monoxide and hydrogen fractions in these examples.

F. Gas Composition

The relative amounts of carbon monoxide and hydrogen which may be initially present in the syngas mixture are variable, and these amounts may be varied over a wide range. In general, the mole ratio of CO-to-$H_2$ is in the range from about 20:1 up to about 1:20, preferably from about 5:1 to 1:5, although ratios outside these ranges may also be employed. Particularly in continuous operations, but also in batch experiments, the carbon monoxide-hydrogen gaseous mixtures may also be used in conjunction with up to 50% by volume of one or more other gases. These other gases may include one or more inert gases such as nitrogen, argon, neon and the like, or they may include gases that may, or may not, undergo reaction under CO-hydrogenation conditions such as carbon dioxide, hydrocarbons such as methane, ethane, propane and the like, ethers such as dimethyl ether, methylethyl ether and diethyl ether, alkanols such as methanol and acid esters such as methyl acetate.

In all syntheses, the amount of carbon monoxide and hydrogen present in the reaction mixture should be sufficient to satisfy the stoichiometry of eq (1)→(3).

G. Product Distribution

As far as can be determined, without limiting the invention thereby, the ruthenium-catalyst one-step CO-hydrogenation process disclosed herein leads to the formation of three classes of primary products, namely the methanol, ethanol and ethylene glycol ester derivatives of the corresponding co-reactant carboxylic acid. In the case then where acetic acid is the co-reactant, the principal products are methyl acetate, ethyl acetate and ethylene glycol diacetate. Minor by-products detected in the liquid product fraction include small amounts of water, glycol monoacetate, propyl acetate and dimethyl ether. Carbon dioxide, methane and dimethyl ether may be detected in the off-gas together with unreacted carbon monoxide and hydrogen.

H. Mode of Operation

The novel process of this invention can be conducted in a batch, semi-continuous or continuous fashion. The catalyst may be initially introduced into the reaction zone batchwise, or it may be continuously or intermittently introduced into such a zone during the course of the synthesis reaction. Operating conditions can be adjusted to optimize the formation of the desired ester product, and said material may be recovered by methods well known in the art, such as distillation, fractionation, extraction and the like. A fraction rich in ruthenium catalyst components may then be recycled to the reaction zone, if desired, and additional ester products generated by CO-hydrogenation.

I. Identification Procedures

The products of CO-hydrogenation have been identified in this work by one or more of the following analytical procedures, viz, gas-liquid phase chromatography (glc), infrared (ir), mass spectrometry, nuclear magnetic resonance (nmr) and elemental analyses, or a combination of these techniques. Analyses have, for the most part, been by parts by weight, all temperatures are in degrees centigrade and all pressures in pounds per square inch gauge (psi).

CO-CATALYST COMPOSITIONS

The improvement here to the use of ruthenium catalyst precursors, useful in the conversion of carbon monoxide-hydrogen mixtures to methanol, ethanol, and glycol ester derivatives, consists of employing one or more suitable ruthenium oxide, salt and/or carbonyl or other derivative species in combination with one or more quaternary aryl-containing phosphonium salt co-catalysts.

The specific class of co-catalyst found useful here in this invention consists of a quaternary phosphonium salt wherein the phosphorous is bonded to one or more aryl or alkaryl radicals each containing from 6 to 20 carbon atoms. Said phosphonium salt must contain at least one aryl or alkaryl group attached to the phosphorus atom in the quaternary structure. Preferably at least two of the organic radicals bonded to the phosphorus atom have aryl function, and most often three or four of said radicals are aryl in chemical character.

Suitable quaternary phosphonium salts are those which are substantially inert under the CO-hydrogenation conditions and which have the formula:

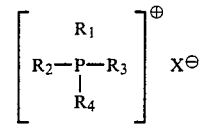

where $R_1$, $R_2$, $R_3$ and $R_4$ are organic radicals bonded to the phosphorus atom with at least one of said radicals being aryl, and X is an anionic species, preferably of a carboxylic acid. More often at least two radicals designated by the R groups above are aryl or alkaryl, and most often three or four radicals have aryl character. Usually the aryl group is phenyl or alkyl substituted phenyl radicals. The alkyl substitutent on the phenyl group may include methyl, ethyl, n-butyl, iso-butyl, octyl, 2-ethylhexyl, dodecyl, etc. radicals.

When $R_1$, $R_2$, $R_3$, or $R_4$ are other than aryl or alkaryl they are preferably aliphatic organic radicals containing 1-20 carbon atoms in a branched or linear alkyl chain. More often said aliphatic radicals contain 1-10 carbon atoms, and may include methyl, ethyl, 2-ethylhexyl, n-heptyl, dodecyl, etc.

The corresponding quaternary phosphonium hydroxides, nitrates and halides, such as the corresponding chlorides, bromides and the iodides, may also be satisfactory in this instance.

Greatly preferred quaternary aryl or alkaryl phosphonium salt co-catalyst species include tetraphenyl phosphonium salts, particularly the acetate salts, and alkyl triphenyl phosphonium salts, particularly methyltriphenyl phosphonium acetate and heptyltrtiphenyl phosphonium acetate.

It has been found that when said aryl or alkaryl phosphonium salt co-catalyst species are employed with the class of ruthenium catalyst described, supra, for the conversion of syngas to methanol, ethanol and glycol ester derivatives, the following advantages accrue:

(1) There is improved selectivity to the most desired glycol ester products relative to the total amount of methanol and ethanol ester derivatives formed.

(2) Considerably less carbon dioxide appears in the off-gas composition.

These advantages for the ruthenium-aryl or alkaryl phosphonium salt combinations are particularly significant when the runs data are compared with ruthenium-quaternary phosphonium or ammonium salt-combinations in which all the radical groups attached to the phosphorus or nitrogen are aliphatic in nature. Said advantages are illustrated by the example outlined below.

The amount of phosphonium quaternary salt employed in this invention may be varied over a wide range of concentration, ranging from about 0.1 to at least $10^2$ moles of salt per gm atom of ruthenium in the reaction mixture. The preferred ratios are about 5–15 moles of phosphonium salt co-catalyst species per mole of ruthenium catalyst.

dioxide materially detracts from overall yields of wanted useful products.

Here the experimental data in nos. 1–5 illustrate the improved performance of the soluble ruthenium catalyst combinations with the quaternary aryl or alkaryl phosphonium salt co-catalyst, while experiments 6 and 7 provide reference data for the ruthenium-quaternary alkyl phosphonium and ammonium salt co-catalyst combinations disclosed previously in the copending application.

TABLE I

| Run[a] | Catalyst Composition | LIQUID PRODUCT COMPOSITION (wt %) | | | | GLYCOL[b] SEL (wt %) | OFF - GAS COMPOSITION (%) | | | |
|---|---|---|---|---|---|---|---|---|---|---|
| | | MeOAc | EtOAc | $(CH_2OAc)_2$ | $(CH_2)_2OAcOH$ | | $H_2$ | CO | $CO_2$ | $CH_4$ |
| 1 | $RuCl_3$—9HpPh$_3$POAc[c] | 44.9 | 6.0 | 5.77 | | 11.3 | 18.8 | 40.4 | 12.1 | 25.6 |
| 2 | $RuCl_3$—9MePh$_3$POAl | 46.8 | 8.1 | 5.45 | | 9.9 | 20.1 | 44.6 | 8.0 | 25.7 |
| 3 | $RuCl_3$—9Ph$_4$POAc | 47.6 | 8.0 | 4.75 | | 8.5 | 19.5 | 40.3 | 10.7 | 25.4 |
| 4 | $RuCl_3$—9MePh$_3$POH | 49.1 | 6.5 | 5.81 | | 10.4 | 21.2 | 42.1 | 9.0 | 24.8 |
| 5 | $RuCl_3$—9HpPh$_3$POAc[c,d] | 44.7 | 5.7 | 4.14 | 4.30 | 16.7 | 50.7 | 32.0 | 14.6 | 0.2 |
| 6 | $RuCl_3$9Bu$_4$POAc | 68.4 | 6.0 | 5.14 | 0.84 | 8.0 | 44.1 | 31.2 | 19.3 | 3.0 |
| 7 | $RuCl_3$—9Me$_4$NOAc | 61.3 | 6.6 | 4.90 | 0.3 | 7.7 | 36.4 | 22.9 | 32.4 | 5.2 |

[a]Run Charge: RuCl$_3$, 3.75 mmole; [P]/[Ru] = 9; HOAc, 50 gm. Run Conditions: 1:1, CO/H$_2$; 430 atm; 220° C., 18 hr.
[b]Glycol Selectivity, Basis: [(CH$_2$OAc)$_2$ + (CH$_2$)$_2$OAcOH]/[MeOAc + EtOAc] × $10^2$
[c]Hp = n-HEPTYL.
[d]Run over 2 days.

EXAMPLE I

To a degassed sample of acetic acid (50 gm) contained in a glass-lined reactor, equipped with pressurizing, heating and means of agitation is added under a nitrogen environment, ruthenium(III) chloride, hydrate, (1.04 gm, 3.8 mmole) and heptyltriphenyl phosphonium acetate salt (34 mmole). The reactor is sealed, flushed with CO/H$_2$, and pressurized to 136 atm with CO/H$_2$ (1:1). The mixture is heated to 220° C. with rocking, the pressure raised to 438 atm by CO/H$_2$ addition from a larger surge tank, and the reactor held at temperature for 18 hours. The pressure in the reaction is maintained at about 430 atm by incremental additions of CO/H$_2$ from the surge tank. On cooling, a typical gas sample is taken and analyzed, and the excess gas removed. The reddish-brown liquid product (68gm) shows no evidence of a solid phase. Analysis of the liquid product fraction shows the presence of:

44.9 wt/methyl acetate
6.0 wt/ethyl acetate
5.8 wt/ethylene glycol diacetate

The ethylene glycol diacetate fraction is recovered from the crude liquid product by fractional distillation.

EXAMPLES 2–7

Following the synthesis of Example 1, ruthenium chloride in combination with a variety of tetra-aryl, alkyl-aryl and tetra-alkyl phosphonium salt and hydroxide co-catalyst species, solubilized in acetic acid co-catalyst, are employed in the conversion of syngas to methyl acetate, ethyl acetate and glycol monoacetate and diacetate. Runs data are summarized in Table I.

The following advantages accrue from the use of the tetraphenyl phosphonium acetate, methyltriphenyl acetate, heptyltriphenyl phosphonium acetate and heptylphenyl phosphonium hydroxide co-catalyst species:

(1) Improved selectivity to the most desired glycol acetate products relative to the total methyl plus ethyl acetates formed (see column 7, Examples 1–5).

(2) Considerably less carbon dioxide off-gas present in the typical off-gas samples. The advantages of producing less CO$_2$ are apparent to those skilled in the art since the production of the relatively useless carbon Finally, the invention is advantageous in that numberous substitutions, modifications and changes can be made without departing from the inventive concept. However, the scope of the subject invention may best be understood by examining the claims, which follow, read in conjunction with the preceding specification.

I claim:

1. In a process for the concurrent synthesis of alkanol and vicinal glycol esters from mixtures of carbon monoxide and hydrogen which comprises the following steps:
   (a) contacting said mixtures of carbon monoxide and hydrogen with a liquid medium containing one or more aliphatic carboxylic acids and a ruthenium-containing catalyst and a co-catalyst species,
   (b) heating said reaction mixture to a temperature of between about 100° C. and 350° C., at superatmospheric pressures of 500 psi or greater with sufficient carbon monoxide and hydrogen to satisfy the stoichiometry of the desired ester syntheses, until substantial formation of the desired esters of the alkanols and vicinal glycols has been achieved,
   (c) isolating said esters contained therein;
   (d) the improvement which comprises utilizing as said co-catalyst species a quaternary aryl or alkaryl phosphonium salt whereby the selectivity to the vicinal glycol esters relative to the alkanol esters is increased.

2. The process of claim 1 wherein the ruthenium-containing catalyst is a ruthenium oxide.

3. The process of claim 2 wherein the ruthenium oxide is selected from the group consisting of ruthenium(IV) dioxide, ruthenium(IV)dioxide hydrate and ruthenium(VIII) tetraoxide.

4. The process of claim 1 wherein the ruthenium-containing catalyst is the salt of a carboxylic acid.

5. The process of claim 4 wherein the ruthenium salt is selected from the group consisting of ruthenium acetate, ruthenium propionate, ruthenium butyrate and ruthenium trifluoroacetate.

6. The process of claim 1 wherein the ruthenium-containing catalyst is the salt of a mineral acid.

7. The process of claim 6 wherein the ruthenium salt is selected from the group consisting of ruthenium chloride hydrate, ruthenium bromide and anhydrous ruthenium chloride.

8. The process of claim 1 wherein the ruthenium-containing catalyst also contains one or more Group VB tertiary donor ligands.

9. The process of claim 8 wherein the Group VB tertiary donor ligands are selected from the group consisting of triphenylphosphine, tri-n-butylphosphine, triphenylphosphite, triethylphosphite, trimethylphosphine, triphenylarsine, trimethylamine, triethylamine, tripropylamine, and tri-n-octylamine.

10. The process of claim 1 wherein the carboxylic acid co-reactant is an aliphatic carboxylic acid of 1 to 12 carbon atoms.

11. The process of claim 10 wherein the aliphatic carboxylic acid is selected from the group consisting of acetic acid, propionic acid and butyric acid.

12. The process of claim 10 where the carboxylic acid co-reactant is a substituted aliphatic carboxylic acid wherein said substituent is selected from the group consisting of lower alkoxy, chloro, fluoro, cyano, alkylthio, and amino.

13. The process of claim 12 wherein the substituted aliphatic carboxylic acid is selected from the group consisting of trifluoroacetic acid, dichloroacetic acid and monofluoroacetic acid.

14. The process of claim 1 wherein the ruthenium catalyst is residual catalyst from previous syntheses of alkanol and vicinal glycol esters from $CO/H_2$ mixtures.

15. The process of claim 1 wherein the co-catalyst is a tetraphenyl phosphonium quaternary salt.

16. The process of claim 15 wherein the quaternary phosphonium salt is an acetate salt.

17. The process of claim 1 wherein the co-catalyst salt is an alkyl triphenyl phosphonium quaternary salt.

18. The process of claim 17 wherein the quaternary phosphonium salt is an acetate salt.

19. The process of claim 17 wherein the alkyl group contains 1–10 carbon atoms.

20. The process of claim 19 wherein the quaternary phosphonium salt is an acetate salt.

* * * * *